(12) United States Patent
Larsson

(10) Patent No.: US 9,795,629 B2
(45) Date of Patent: Oct. 24, 2017

(54) AQUEOUS SOLUTION COMPRISING A MACROMOLECULAR CONJUGATE OF HEPARIN FOR THE TREATMENT OF BLOOD VESSELS

(71) Applicant: CORLINE SYSTEMS AB, Uppsala (SE)

(72) Inventor: Rolf Larsson, Uppsala (SE)

(73) Assignee: CORLINE SYSTEMS AB, Uppsala (SE)

( * ) Notice: Subject to any disclaimer, the term of this patent is extended or adjusted under 35 U.S.C. 154(b) by 0 days.

(21) Appl. No.: 14/366,483

(22) PCT Filed: Dec. 17, 2012

(86) PCT No.: PCT/SE2012/051410
§ 371 (c)(1),
(2) Date: Jun. 18, 2014

(87) PCT Pub. No.: WO2013/095270
PCT Pub. Date: Jun. 27, 2013

(65) Prior Publication Data
US 2014/0349963 A1    Nov. 27, 2014

(30) Foreign Application Priority Data

Dec. 22, 2011 (SE) .................... 1151266-2

(51) Int. Cl.
*A61K 31/727* (2006.01)
*A01N 1/02* (2006.01)
*A61K 47/48* (2006.01)
*A61L 27/34* (2006.01)
*A61L 27/54* (2006.01)
*A61L 33/00* (2006.01)

(52) U.S. Cl.
CPC .......... *A61K 31/727* (2013.01); *A01N 1/0226* (2013.01); *A61K 47/48238* (2013.01); *A61L 27/34* (2013.01); *A61L 27/54* (2013.01); *A61L 33/0011* (2013.01)

(58) Field of Classification Search
None
See application file for complete search history.

(56) References Cited

U.S. PATENT DOCUMENTS

| | | | |
|---|---|---|---|
| 5,529,986 A | 6/1996 | Larsson et al. | |
| 7,504,113 B2 | 3/2009 | Lassila et al. | |
| 2008/0014239 A1 | 1/2008 | Lassila et al. | |
| 2009/0098174 A1* | 4/2009 | Larsson ........................ | 424/422 |

FOREIGN PATENT DOCUMENTS

| | | |
|---|---|---|
| EP | 1832289 A2 | 9/2007 |
| EP | 1832289 A3 | 12/2007 |
| WO | 93/05793 A1 | 4/1993 |
| WO | 2007/004975 A1 | 1/2007 |
| WO | WO-2009134054 A2 | 11/2009 |

OTHER PUBLICATIONS

Cabric et al. ("A New Method for Incorporating Functional Heparin onto the Surface of Islets of Langerhans" Tissue Engineering, vol. 14 (2), 2008).*
Liao et al. (Covalent linkage of heparin provides a stable anti-coagulation surface of decellularized porcine arteries; J. Cell Mol Med, 2009; 13(8B): 2736-2743).*
Mayfield Brain and Spine (http://www.mayfieldclinic.com/PE-AneurUn.htm , available Nov. 8, 2003).*
Reenan (AMA Journal of Ethics; Indications for Bypass Surgery, Feb. 2004, vol. 6 (2)).*
Estridge et al. (Basic Medical Laboratory Techniques, p. 238, 2000).*
San Antonio et al. (Mapping the Heparin Binding Sites on Type I collagen Monomers and fibrils, The Journal Of Cell Biology; vol. 125(5), 1994).*
Extended European Search Report dated Jun. 29, 2015, corresponding to Application No. 12859003.1-14551 / Patent No. 2793909, PCT/SE2012051410.
International Search Report for PCT/SE2012/051410, mailed Apr. 3, 2013; ISA/SE.

* cited by examiner

Primary Examiner — James H Alstrum Acevedo
Assistant Examiner — Tara Martinez
(74) Attorney, Agent, or Firm — Harness, Dickey & Pierce, P.L.C.

(57) ABSTRACT

The present invention relates to a solution for treating blood vessels where the solution comprises a heparin conjugate. The invention further relates to the use of the conjugate as a medicament and a method of coating tissue using the conjugate.

10 Claims, 1 Drawing Sheet

US 9,795,629 B2

Figure 1:
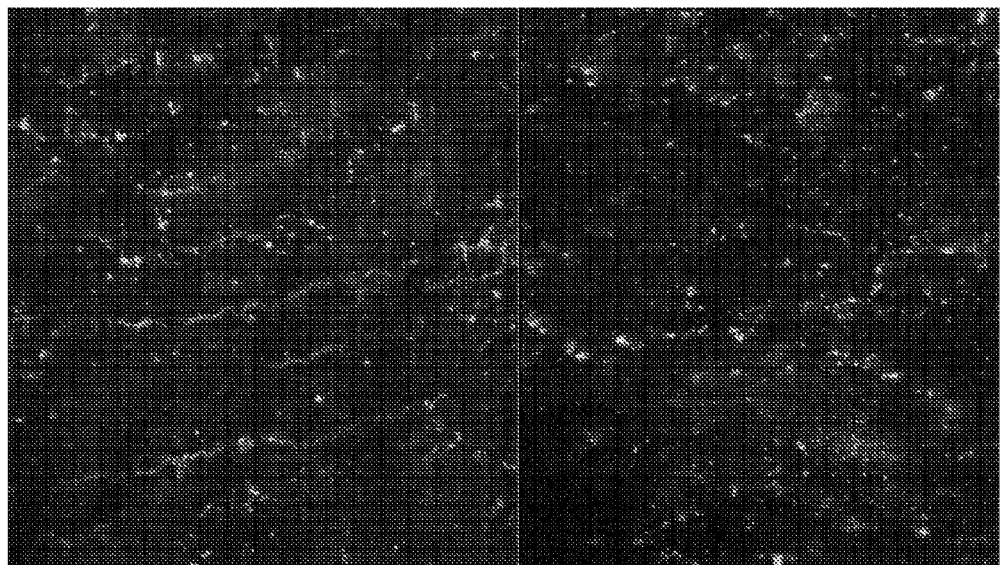

AQUEOUS SOLUTION COMPRISING A MACROMOLECULAR CONJUGATE OF HEPARIN FOR THE TREATMENT OF BLOOD VESSELS

FIELD OF THE INVENTION

The present invention relates to a buffer solution comprising a macromolecular conjugate of heparin for the treatment of blood vessels, a medicament for the treatment of blood vessels and a method of coating blood vessels.

BACKGROUND

Circulating blood is maintained in a delicate state of balance as long as it is flowing in undisturbed blood vessels lined by an intact endothelium. However, there are numerous situations where this balance is adversely affected so as to induce thrombosis, a life-threatening event that remains the number one man-killer if left untreated. On the other hand, if the reactions involved in the onset of thrombosis are set aside by too efficient inhibition excessive and life-threatening bleeding may occur.

It is generally accepted that the vascular wall facing blood should be covered by an undamaged monolayer of endothelial cells. This cell layer is covered by network of membrane-bound proteoglycans and glycoproteins, referred to as the endothelial glycocalyx. Over the last decade, the endothelial glycocalyx has increasingly been appreciated as an intravascular compartment that protects the vessel wall against pathogenic insults. Damage to the endothelial glycocalyx has been shown to enhance adhesion of leucytes and platelets to the vascular endothelium, and also to induce endothelial dysfunction due to disturbed mechanotransducing effects. Significant disturbance of the endothelial glycocalyx has been reported to be associated with e.g. diabetes, ischemia/reperfusion and atherosclerosis.

Today vessel wall damages caused by dilation or other surgical procedures and diseases are treated by systemic administration of various drugs.

Heparin has a long record as a clinically accepted anti-coagulant by acting as a potent accelerator of antithrombin, a naturally occurring protein in blood that is capable of inhibiting a number of coagulation enzymes including thrombin. Hirudin is an example of a direct inhibitor of thrombin. The use of heparin or hirudin is associated with a less than negligible risk of bleeding.

A macromolecular conjugate composed of multiple heparin chains covalently linked to an inert main chain has been utilized for modifying both artificial (WO93/05793) and biological surfaces (WO00/45837) in such a way that these surfaces present permanently surface-bound heparin so as to mimic the chemical constitution of the blood vessel endothelium, which carries surface localised heparan sulphate.

SUMMARY OF THE INVENTION

The object of the present invention is to present a composition for administration to blood vessels for efficient inhibition of thrombogenic reactions. Said reactions may be induced by contact of blood with blood vessel lesions exposing collagen, fibrin, and activated cells deposited on the vascular lesion presenting surface structures that are not compatible with blood.

In a first aspect the present invention relates to an aqueous solution comprising water and an effective amount of a macromolecular heparin conjugate for use in the treatment of blood vessels in vitro. The solution is defined in claim 1.

In another aspect the present invention relates to the use of a macromolecular heparin conjugate as a medicament for the treatment of blood vessel damages or diseases.

In a third aspect the present invention relates to an in vitro method of coating the endothelial surface of a blood vessel prior to transplanting the vessel or an organ containing blood vessels into a patient comprising bringing the blood vessel surfaces in contact with an aqueous solution comprising water and an effective amount of a macromolecular heparin conjugate.

In a fourth aspect the present invention relates to a method of treating a patient comprising bringing the surface of a damaged blood vessel in contact with the aqueous solution comprising water and an effective amount of a heparin conjugate.

In a fifth aspect the invention is provides a method of transplanting an organ into a patient.

Preferred embodiments of the present invention are as defined in the dependent claims and are hereby incorporated into the description.

SHORT DESCRIPTION OF THE FIGURES

FIG. 1 discloses the results from confocal microscopy of pig artery showing binding of Streptavidin-Cy5 (red) to biotinylated CHC adsorbed to the vasculature.

The picture to the left shows an artery perfused with CHC and the picture to the right an artery perfused with PBS.

Figure 2:
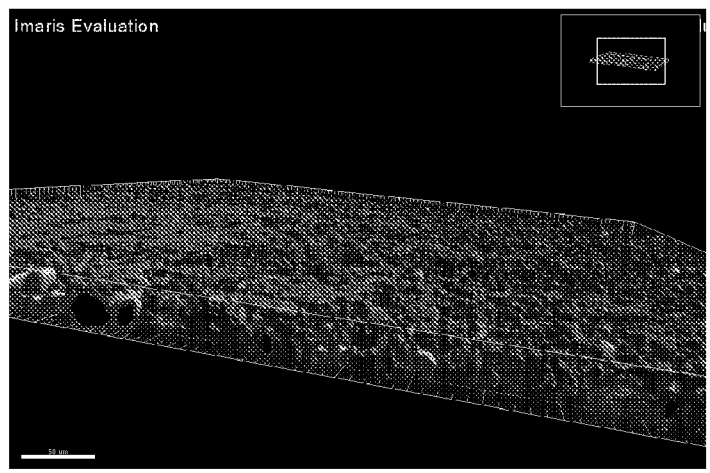

FIG. 2 discloses Imaris evaluation of binding of Streptavidin-Cy5 to CHC-biotin attached to a blood vessel.

Figure 3:
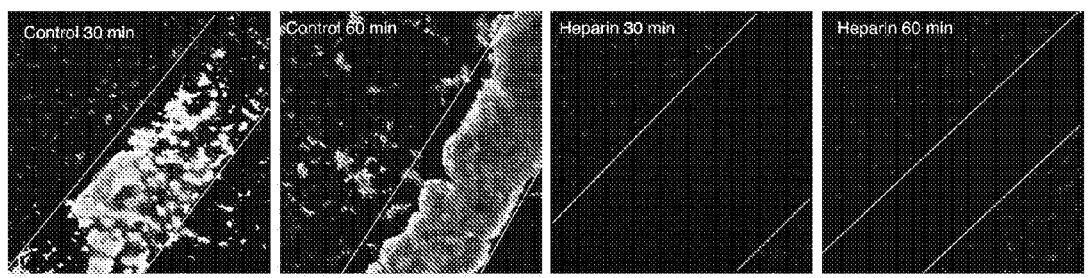

FIG. 3 discloses the results from confocal microscopy after 30 and 60 minutes of treatment with CHC (to the left) and control (to the right).

DETAILED DESCRIPTION OF THE INVENTION

In the present application the term "sulphated glycosaminoglycans" refers not only to the substances, which are normally included in the term, such as e.g. heparin, heparan sulphate, dermatan sulphate and chondroitin sulphate, but also fragments and derivatives of these substances which are functional for the purpose.

Heparan sulphate expressing antithrombin binding sites is a major component of the endothelial glycocalyx. According to the present invention a macromolecular conjugate of heparin is used to restore the endothelial glycocalyx of isolated blood vessels and blood vessels contained in organs so as to reduce damage that may have occurred by ischemic and mechanical processing.

The present invention presents a macromolecular glycosaminoglycan conjugate that can be used as a medicament to treat vessel damages or disease or to treat vessels prior to transplantation.

A healthy blood vessel wall is covered by a coherent layer of endothelial cells having a layer of carbohydrates called glycocalyx facing the blood flow. An important component in glycocalyx is heparin sulphate which in collaboration with antithrombin minimizes the generation of thrombotic reactions. Different forms of blood vessel damages, or diseases, may affect the properties of the glycocalyx in a negative way, for example ischemia.

A macromolecular heparin conjugate according to the invention shows promising results concerning the binding effect to components found on a damaged blood vessel wall such as collagen, fibrin and activated thrombocytes. When the heparin conjugate of the present invention have bound to the blood vessel surface and the bound heparin conjugate on the surface cooperates with antithrombin a significant decrease of thrombogenic reactions is seen.

One application according of the present invention is to use the heparin conjugate to treat organs for transplantation or to treat patients whose blood vessels may be damage during a medical or surgical treatment. In another embodiment the present invention may be used to treat blood vessels in vitro when removed from a patient and before transplanting the vessels or organ containing the vessels into the a patient. The conjugate is administrated to the vessel or the patient dissolved in an aqueous solution in a concentration range of 0.001-10 mg/ml, such as 0.001 mg/ml or more, or 0.01 mg/ml or more, or 0.1 mg/ml or more, or 1 mg/ml or more, or 3 mg/ml or more, or 10 mg/ml or less, or 7 mg/ml or less, or 5 mg/ml or less. The aqueous solution could be a buffer solution and the buffer could be any physiologic buffer for example a phosphate buffer, PBS.

It was discovered, quite surprisingly, that a macromolecular conjugate composed of multiple heparin molecules binds to collagen strongly enough to abrogate the thrombogenic character of collagen adsorbed onto a surface in contact with blood, see Example 2. This binding and protective effect of the macromolecular heparin conjugate stands in sharp contrast to ordinary, commercially available heparin intended for intravenous administration, which has no effect in this regard. Similarly, it was found that a macromolecular conjugate composed of multiple heparin molecules binds to fibrin but not to fibrinogen, see Example 3.

A macromolecular conjugate of heparin according to the invention comprises multiple non-fractionated glycosaminoglycan (GAG), preferably heparin, molecules preferably covalently linked, preferably via single-point attachment, to an inert main chain. The number of GAG molecules per conjugate should be at least ten but preferably between 20 and 100, that is 20 or more, or 50 or more or, or 70 or more, or 100 or less, or 80 or less. A certain fraction of the GAG molecules will be engaged in binding to the biological substrate while the remaining GAG molecules, not engaged in binding, are free to exert the biological activity of GAG. Due to multiple binding between the GAG molecules and the substrate having affinity for GAGs, the binding strength of the macromolecular conjugate of GAGs will exceed that of ordinary GAG resulting in superior performance. In order to obtain the advantageous combination of strong binding and retained biological activity it is preferable that multiple GAG chains are oriented in such a way that they are free to interact with the substrate that has an affinity for GAGs and especially heparin. The GAG should be attached to the main chain preferably by single-point attachment. One preferred embodiment of a macromolecular conjugate of GAG is the Corline Heparin Conjugate (CHC), which is composed of approximately 70 heparin molecules linked to the inert main chain (Obtainable from Corline Systems AB, Uppsala, Sweden). The number of heparin molecules should preferably be between 65 and 75 per chain. The preferred conjugate is described in U.S. Pat. No. 5,529,986 which is hereby incorporated by reference.

The macromolecular conjugate is an at least substantially water-soluble, biologically active conjugate (macromolecule), preferably in substantially pure form, comprising a substantially straight-chained organic homo- or heteropolymer having a number of functional groups distributed along the polymer backbone chain, via which groups of at least about 10 molecules from the group of sulphated glycosaminoglycans (GAG) in a non-active part thereof are anchored through covalent bonds.

Such a conjugate may conceptually be described as a synthetic proteoglycan, the relative composition of which may be varied in a controllable way and adapted to the intended application.

The substantially linear polymer chain which is to function as the main chain for the glycosaminoglycan residues should, of course, be substantially biologically inert after the coupling of the glycosaminoglycan or -glycans in question, in the sense that it should be devoid of at least interfering biological activity. As is readily understood, in order to permit coupling of a plurality of glycosaminoglycan residues the main chain should be provided with a number of functional groups, such as e.g. amino, amide, sulphate, vinyl, carbonyl, nitro, thiol, hydroxyl or carboxyl groups, distributed along the chain and capable of, after optional modification, coupling of the glycosaminoglycan, either directly or via a coupling sequence. It is in this context to be noted that the GAG in question, depending on the method of producing the conjugate, may still have the terminal residue of its natural conjugate protein associated thereto, and that the binding then, of course, advantageously will take place via e.g. an amino acid in such a residue.

Further, the main chain, preferably a polymer chain, should preferably have a good solubility in water. At least it should, in accordance with what has previously been said about the conjugate, be at least substantially water-soluble after the coupling of the glycosaminoglycan groups. Specific polymer chains, which may be suitable for the purposes of the invention will readily be apparent to the skilled person after having taken part of the general inventive concept. This is, of course, also the case for the degree of branching on the polymer chain that may be permitted within the scope of the expression "substantially linear".

Preferably the polymer chain is a natural or synthetic polypeptide, polysaccharide or an aliphatic polymer. In one embodiment the main chain is an inert aliphatic compound. As specific non-limiting examples the main chains could be polylysine, polyornithine, chitosan, polyimine and polyallylamine, starch, cellulose, chitin, hyaluronan, polyesters, polyethers, polyamides, polyamines, polyurethanes or combinations or mixtures thereof.

With regard to the fact that it is usually desired that the glycosaminoglycan will maintain its biological activity after the binding to the polymer main chain, it is preferred that each glycosaminoglycan molecule is bound terminally and by only a single bond to the main polymer. For example, the glycosaminoglycan may be bound to the main chain via an amino acid, and then preferably a terminal amino acid, but also free amino groups of a glucosamine unit may be used. The latter may exist free as such or may have been liberated through desulphation or deacetylation.

Particularly in the case that an amino-functional polymer is used as the main chain, it may in some cases, especially when the main chain is sparsely substituted with glycosaminoglycans, be favourable to block the remaining free amino groups, which, for example, may be executed by acetylation. An alternative approach might be to substitute a desired number of amino groups with e.g. methyl groups before attaching the glycosaminoglycans.

In a preferred embodiment of the invention, the macromolecular heparin conjugate has a molecular weight higher than 70 kDa. Preferably, the molecular weight of the macromolecular heparin conjugate is higher than 200 kDa, more preferably higher than 400 kDa, and even more preferably higher than 600 kDa.

APPLICATIONS OF THE INVENTION

One application of the present invention is for coating collagen. For example, three dimensional matrices of collagen or gelatine (hydrolysed collagen) are hydrated by immersion in a phosphate buffer solution (PBS) for at least one hour followed by immersion in PBS supplemented with CHC at a concentration ranging from 0.01-10 mg/ml for a period of 5 to 60 minutes and then careful rinsing three times with PBS.

Another application refers to coating of tissue samples such as the endothelial surface of a blood vessel. Tissue specimens (exposing collagen) intended for implantation into the human body are immersed in a PBS solution supplemented with CHC at a concentration ranging from 0.001-10 mg/ml, such as 0.001 mg/ml or more, or 0.01 mg/ml or more or 0.1 mg/ml or more, or 1 mg/ml or more, or 3 mg/ml or more, or 10 mg/ml or less, or 7 mg/ml or less, or 5 mg/ml or less, for a period of 5 to 120 minutes and then careful rinsing three times with PBS.

Another application refers to a medicament comprising a heparin conjugate comprising a main chain of an inert aliphatic chain and at least one heparin linked to the main chain as a medicament for the treatment of blood vessel damages or diseases. In another embodiment the heparin conjugate comprises heparin molecules in the interval 10 to 100. The blood vessel damage could be caused by dilation of the blood vessel or other surgical procedures and the blood vessel disease could be ischemia. The conjugate could be dissolved in a sterile physiological salt solution and administered systemically to allow the conjugate to be dissolved in blood and optionally bind to vascular lesions where collagen and/or fibrin is exposed in order to block thrombus formation that may be induced at such lesions. The salt solution could be any buffer solution such as PBS and the concentration of the heparin conjugate could be ranging from 0.001-10 mg/ml, such as 0.001 mg/ml or more, or 0.01 mg/ml or more or 0.1 mg/ml or more, or 1 mg/ml or more, or 3 mg/ml or more, or 10 mg/ml or less, or 7 mg/ml or less, or 5 mg/ml or less.

Myocardial reperfusion injury is a multifactorial, still poorly understood, syndrome associated with coronary heart disease being the leading cause of death world-wide. Reperfusion injury is also an important factor to consider in association with transplantation of organs. Ischemia induces vascular damage and a hypothesis is that such vascular lesions may initiate platelet activation and generation of thrombin at blood exposure during reperfusion. Isolated organs may benefit from perfusion with the heparin conjugate solution of the present invention prior to transplanting the vessel or organ into a patient may be in combination with systemic administration of the conjugate of the present invention in connection with the onset of reperfusion.

The solution is usable in the transplantation of organs to patients, in particular kidneys.

Thus, the invention provides a method of transplanting an organ into a patient, comprising the steps of providing an organ to be transplanted, perfusing the organ with a solution according to any of claims 1-6 in a buffer so as to coat the tissue of the organ with a protective coating, and transplanting the organ to the patient. Suitably the organ is perfused with the solution for a period of time of at least 1 hour, although the period can be longer such as up to 24 hours or even more.

Perfusion is performed by connecting the kidney to a circulation system in which normally about 1 liter of buffered solution is circulated to the organ.

After such perfusion the vessels of the blood vessels in the organ is coated with a protective coating that will prevent ischemia/reperfusion of the transplanted organ.

EXAMPLES

Example 1

The specific biological activity of heparin and CHC, respectively, was assessed by a FXa inhibition assay. Heparin had an activity of 200 IU/ml and CHC had 30 IU/ml.

Example 2—Collagen Surface Modified with CHC

PVC tubings were precoated with collagen (Bovine collagen type I, Purecol) by rotating tubings with PBS supplemented with collagen (60 µg/ml) during three hours and divided into three groups. Group I received no further treatment, group II was incubated with PBS supplemented by heparin (50 µg/ml) for 30 minutes and group III was incubated with PBS supplemented with CHC (50 µg/ml) for 30 minutes. Tubing loops were prepared from each group and rotated at 37° C. with freshly sampled human blood without any anticoagulant. Group I and II induced the formation of solid clots within thirty minutes with total consumption of the platelets. No clotting occurred in group III, and after sixty minutes the platelet count remained at more than 90% of the baseline level. This example shows that CHC, but not heparin, is capable of binding to collagen and thereby transforming the thrombogenic collagen surface into a non-thrombogenic heparin surface.

Example 3—Fibrin Surface Modified with CHC

PVC tubing loops were rotated with human citrated plasma supplemented with $CaCl_2$ (group II) at a concentration that caused visible clotting (fibrin formation) within 20 minutes. After clotting had occurred the tubings were drained and carefully rinsed with PBS and divided into two groups. Group I received no further treatment and group II was incubated with PBS supplemented by CHC (50 µg/ml) for 30 minutes. Tubing loops were prepared from each group and rotated at 37° C. with freshly sampled human blood without any anticoagulant. Group I induced the formation of solid clots within thirty minutes with total consumption of the platelets. No clotting occurred in group II, and after sixty minutes the platelet count remained at more than 90% of the baseline level. This example shows that CHC, but not heparin, is capable of binding to fibrin and thereby transforming the thrombogenic fibrin surface into a non-thrombogenic heparin surface.

Example 4—Perfusion of an Isolated Kidney

In a pig transplantation model, kidneys were obtained from brain dead donor pigs with a weight of 30 kg. After aortic flush with perfusion solution (UW, University of Wisconsin), the kidneys were harvested and placed in a commercial perfusion machine (Organ Assist, NL) where the two kidneys were exposed to a pressure steered pulsatile cold perfusion with machine perfusion solution for a minimum of 2 h at a concentration of 50 µg/ml. One kidney was perfused with a solution comprising CHC.

The consumption of CHC during perfusion of isolated kidneys was monitored using a toluidine blue assay that can be used to detect CHC in the range of 10-50 µg/ml. Experiments with perfusion of kidneys from five pigs have shown that 10-15 mg of CHC bound to the perfused kidneys.

Example 5—Binding of CHC to a Blood Vessel

Segments of arteria iliaca were harvested from a pig that had been brain dead for three hours. After perfusion with PBS (sodium phosphate buffer pH 7.4) one segment was incubated with CHC (Biotinylated CHC, 50 μg/ml in PBS) and another with PBS only. Fluorescent labelled streptavidin (Streptavidin-Cy5 which shows up in red) was used to detect surface attached CHC-biotin. FIG. 1 discloses the results recorded by confocal microscopy shows a distinct uptake of Streptavidin-Cy5 in red on the CHC-biotin sample with very little or no signal from the control sample. Binding of an antibody directed towards von Willebrand Factor (shown in green) was comparable between the two samples.

Computer assisted analysis (Imaris) of the specimen with CHC-biotin further verified binding of CHC to the blood vessel, see FIG. 2.

Example 6—Binding of CHC to Collagen Prevents Platelet Deposition

A confluent layer of endothelial cells (EC) was established on glass slides which had been coated with collagen type I. A wound was created by scraping off the EC cells using a thin tip of a pipett. One test sample was subsequently incubated with CHC (50 μg/ml in PBS buffer) for 30 minutes and then carefully rinsed with PBS. Another sample was used as a control without any further treatment following the scraping.

Both samples were incubated with fresh human blood for 60 minutes using a special device to make sure that blood was flowing over the surfaces. The test specimens were rinsed and fixed with paraformaldehyde and examined by confocal microscopy using a fluorescent antibody (shown in green) directed against CD 62 (p-selectin) being expressed by activated platelets. In the pictures below the wound is outlined by the thin white lines, see FIG. 3. On the control surface a dense layer of activated platelets could be detected (left, denoted Control), whereas no deposition of platelets could be seen on the sample on which CHC had been allowed to bind to collagen (right, denoted Heparin).

The invention claimed is:

1. A method of coating the surface of a blood vessel, the method comprising:
    bringing a blood vessel, wherein collagen or fibrin is exposed on a surface of the blood vessel, in contact with an aqueous solution comprising water and an effective amount of a macromolecular heparin conjugate, wherein the heparin conjugate is a conjugate comprising a main chain of an inert aliphatic compound and at least ten heparin chains linked to the main chain; and
    wherein the heparin conjugate directly binds to the collagen or fibrin exposed on the surface of the blood vessel, and
    wherein the heparin conjugate bound to the collagen or fibrin is biologically active.

2. The method of claim 1, wherein the blood vessel is present in an organ for transplantation.

3. The method according to claim 1, wherein the method is an in vitro method.

4. The method according to claim 1, wherein the number of heparin chains is 50 or more but less than 100.

5. The method according to claim 1, wherein the aqueous solution is a buffer solution.

6. The method according to claim 1, wherein the concentration of the heparin conjugate is between 0.01 and 10 mg/ml.

7. The method according to claim 6, wherein the concentration of the heparin conjugate is between 0.1 mg/ml and 7 mg/ml.

8. The method according to claim 6, wherein the concentration of the heparin conjugate is between 0.01 mg/ml and 5 mg/ml.

9. The method according to claim 6, wherein the concentration of the heparin conjugate is between 0.5 mg/ml and 10 mg/ml.

10. The method according to claim 1, wherein the heparin conjugate directly binds to the fibrin exposed on the surface of the blood vessel.

* * * * *